(12) United States Patent
Eitenmueller

(10) Patent No.: US 8,109,929 B2
(45) Date of Patent: Feb. 7, 2012

(54) MEDICAL INSTRUMENT FOR COAGULATION OF TISSUE

(75) Inventor: Juergen P. Eitenmueller, Castrop-Rauxel (DE)

(73) Assignee: Karl Storz GmbH & Co. KG (DE)

( * ) Notice: Subject to any disclaimer, the term of this patent is extended or adjusted under 35 U.S.C. 154(b) by 810 days.

(21) Appl. No.: 12/171,630

(22) Filed: Jul. 11, 2008

(65) Prior Publication Data

US 2009/0018540 A1    Jan. 15, 2009

(30) Foreign Application Priority Data

Jul. 13, 2007  (DE) .................. 10 2007 034 578

(51) Int. Cl.
*A61B 18/14* (2006.01)
(52) U.S. Cl. .......................... 606/49; 606/40
(58) Field of Classification Search ............ 606/40, 606/41, 49; 600/373; 604/21
See application file for complete search history.

(56) References Cited

U.S. PATENT DOCUMENTS

| | | | |
|---|---|---|---|
| 4,637,392 A * | 1/1987 | Sorochenko | ............ 606/50 |
| 5,403,311 A | 4/1995 | Abele et al. | |
| 5,451,223 A | 9/1995 | Ben-Simhon | |
| 5,460,629 A | 10/1995 | Shlain et al. | |
| 5,702,387 A | 12/1997 | Arts et al. | |
| 6,032,673 A * | 3/2000 | Savage et al. | ............. 128/898 |
| 2006/0069386 A1* | 3/2006 | Dubnack et al. | ............. 606/41 |
| 2006/0241580 A1* | 10/2006 | Mittelstein et al. | ............. 606/41 |
| 2008/0306335 A1* | 12/2008 | Lau et al. | ............. 600/106 |

FOREIGN PATENT DOCUMENTS

| | | |
|---|---|---|
| DE | 3390567 C2 | 12/1985 |
| DE | 9114125 U1 | 1/1992 |
| DE | 69635288 T2 | 7/2006 |
| EP | 0418382 A1 | 3/1991 |

OTHER PUBLICATIONS

Storz Advertising Literature: Storz Brochure "Karl-Storz Endoskope, Laparoscopy", 5th edition Jan. 2005 p. 182.
European Search Report, EP08011892, Sep. 2, 2008, 6 pages.

* cited by examiner

Primary Examiner — Michael Peffley
Assistant Examiner — Thomas Giuliani
(74) Attorney, Agent, or Firm — St. Onge Steward Johnston & Reens LLC

(57) ABSTRACT

A medical instrument for coagulation of tissue has an electrode carrier and, at a distal end of the electrode carrier, an electrode that can be supplied with high-frequency current. The medical instrument also has a stripper arranged directly adjacent to the electrode. The stripper and the electrode can be moved relative to each other in order to remove contaminants from the electrode.

14 Claims, 5 Drawing Sheets

MEDICAL INSTRUMENT FOR COAGULATION OF TISSUE

CROSS REFERENCE TO RELATED APPLICATION

The present application claims priority of German patent application No. 10 2007 034 578.1 filed on Jul. 13, 2007.

BACKGROUND OF THE INVENTION

The invention relates to a medical instrument for coagulation of tissue, comprising an electrode carrier and, at a distal end of the electrode carrier, an electrode that can be supplied with high-frequency current.

Such medical instruments are used, for example in the field of minimally invasive surgery, during a laparoscopy intervention in order to obliterate tissue. The medical instrument is guided through a trocar into an opening in the body of a patient, such that the electrode that can be supplied with high frequency current and is arranged at the distal end of the electrode carrier comes into contact with the tissue to be coagulated and obliterates this tissue.

A medical instrument for coagulation is known, for example, from the company brochure of Karl Storz GmbH & Co., Tuttlingen, "Karl Storz-Endoskope, Laparoskopie", 5th edition, 1/2005, page 182. A medical instrument provided with product number 37370 SC is known from this brochure.

The known medical instrument has an electrode carrier in the form of a coagulation/suction tube, on the distal end of which a tubular electrode made of metal is arranged. At its proximal end, the electrode carrier can be supplied with high-frequency current via a connector piece arranged on a coupling. During the intervention, a suction line can also be joined to the proximal end of the electrode carrier designed as suction tube, such that, for example, blood or fluid is suctioned away from the operating site in the proximal direction.

A disadvantage of this medical instrument is that, during tissue coagulation, contaminants in the form of burnt tissue, for example, deposit themselves on the outer face of the electrode acting as coagulation surface, as a result of which the electrode, over the course of time, is covered with these often tenaciously adhering deposits. These contaminants adhering to the electrode form an insulating layer on the metal electrode surface, such that the effective coagulation surface area of the electrode is reduced or completely eliminated and no longer comes into contact with the tissue to be obliterated. As a result, the medical instrument is unsuitable for further use.

A further disadvantage is that the electrode of the medical instrument covered with contaminants can only be cleaned outside the patient, such that the medical instrument has to be withdrawn from the opening in the patient's body and, after cleaning or replacement of the electrode, has to be inserted back into the opening in the patient's body. This increases the time taken to perform the medical intervention.

Another medical instrument is known from document DE 33 90 567 C2 which is a bipolar coagulator having an electrode at the distal end. The electrode has a helical groove on the outer surface. A stripper is arranged at the outer circumference of the electrode which serves to strip off contaminants from the raised surface areas of the electrode and to displace same into the helical groove in which the contaminants are transported to the proximal side. The electrode is closed at its distal end.

DE 696 35 288 T2 discloses electrosurgical electrodes having a silicone coating which prevents the built-up of coagulated tissue on the electrode and which facilitates the removal of coagulated tissue from the electrode.

U.S. Pat. No. 5,460,629 discloses an electrosurgical instrument having two types of electrodes arranged at its distal end, namely a hook-shaped electrode and two plate-shaped electrodes which are arranged on opposite sides of the hook-shaped electrode. The plate-shaped electrodes can be moved axially relative to the hook-shaped electrode, whereby the plate-shaped electrodes strip off coagulated tissue from the sides of the hook-shaped electrode. Thus, the plate-shaped electrodes are only effective on the side surfaces of the hook-shaped electrode.

U.S. Pat. No. 5,451,223 discloses an electrosurgical scalpel having a blade which has a blade cleaning device. The cleaning device is formed by a metal sleeve, the inner cross-section of which is adapted to the outer cross-section of the blade, and the distal opening of which is configured as a sharp blade. By axially moving the sleeve in forward direction, coagulated tissue adhering to the blade is stripped off.

Finally, EP 0 418 382 A1 discloses an electrosurgical instrument having electrodes to which cleaning elements are assigned which are axially movable relative to the electrodes.

SUMMARY OF THE INVENTION

It is an object of the present invention to improve a medical instrument of the type mentioned at the outset, in such a way that the electrode thereof has a maximum coagulating action throughout the entire duration of the medical procedure.

According to the invention, a medical instrument for coagulation of tissue is provided, comprising an electrode carrier having a distal end, an electrode arranged at the distal end of the electrode carrier which can be supplied with high-frequency current, and a stripper arranged directly adjacent to the electrode, the stripper and the electrode being able to be moved relative to each other in order to remove contaminants from the electrode.

At the distal end of its electrode carrier, the medical instrument has a stripper which is used to remove contaminants adhering to the electrode and which is located in direct proximity to the electrode. According to the invention, a "directly adjacent arrangement" of the electrode and of the stripper is to be understood as meaning that the stripper and the electrode touch, or they are spaced apart from each other in such a way that the electrode and the stripper can interact to remove the contaminants adhering to the electrode. The contaminants adhering to the electrode are removed by means of the stripper and the electrode being moved relative to each other and by the stripper stripping the contaminants off from the electrode. The relative movement of the stripper and the electrode can be axial or transverse to the axial direction. In this way, it is advantageously ensured that the electrode of the medical instrument can be cleaned during the medical intervention, as a result of which the insulating layer of contaminants that forms on the electrode during the intervention is removed.

It is also advantageous that the tissue coagulation process does not have to be interrupted in order to free the electrode of the contaminants adhering to its coagulation surface. Instead, the tissue obliteration and the cleaning of the electrode can be performed simultaneously, since the stripper and the electrode are arranged directly adjacent to each other, and the stripper does not have to be moved toward the electrode in order to clean this.

It is also advantageous that the medical intervention is particularly time-saving, since the electrode covered with contaminants does not have to be removed from the opening in the patient's body. Instead, the cleanable electrode at the distal end of the medical instrument allows the operator to work continuously without interruptions.

In a preferred embodiment of the invention, the stripper and the electrode can be moved relative to each other transversely with respect to a longitudinal direction of the electrode carrier.

This measure has the advantage that the coagulation does not have to be interrupted during cleaning of the electrode, since the stripper and the electrode move transverse to the longitudinal direction of the electrode carrier and thus transverse to the electrode, and the electrode is not temporarily completely covered by the stripper, and instead a constantly large electrode surface area is available for coagulation. Moreover, the structure of the medical instrument is advantageously particularly stable, since the absence of axial displaceability of the electrode and of the stripper relative to each other prevents axial lifting of the distal end of the stripper from the electrode, due to lumpy elevated contaminants on the electrode surface, and thus possible breaking of the stripper.

In another preferred embodiment of the invention, the stripper extends in the longitudinal direction at least along a partial area of the electrode.

This measure has the effect that the stripper and its active cleaning surface directed towards the electrode are of sufficiently large dimensions, as a result of which cleaning of the electrode over a large surface area is possible. In this way, the cleaning of the electrode is performed particularly quickly by the stripper. The stripper preferably extends along the full length of the electrode.

In another preferred embodiment of the invention, the stripper tapers distally.

This measure has the advantage that the effective coagulation surface area of the electrode is not unnecessarily reduced in size by the stripper, such that the coagulation surface area of the electrode is particularly large and the medical intervention can be performed speedily.

In another preferred embodiment of the invention, the stripper engages around a distal end of the electrode.

This measure has the advantage that the stripper is always arranged in a stable position on the electrode, since the for example hook-shaped engagement of the distal end of the electrode by the distal end region of the stripper prevents lifting and/or breaking of the stripper from the electrode by contaminants that are not smooth but adhere in lumps on the surface of the electrode. Moreover, this embodiment of the stripper advantageously permits a sufficiently large contact area of the stripper on the electrode surface along its full extent, such that contaminants adhering tenaciously to the electrode can also be removed by the stripper.

In another preferred embodiment of the invention, the stripper has a scraper edge facing towards the electrode and designed as a blade.

This measure has the effect that the action of the stripper cleaning the electrode is achieved by the scraper edge scraping across the electrode surface, as a result of which the tissue adhering to the electrode adjacent to the scraper edge is scraped off the electrode surface and thus removed. In this way, particularly thorough cleaning of the electrode by the stripper is achieved. The embodiment of the scraper edge as a blade advantageously permits targeted removal of the contaminants in a defined area along the cutting edge of the blade.

In another preferred embodiment of the invention, the stripper has two scraper edges facing towards the electrode and each designed as a blade.

This measure has the advantage that, depending on the arrangement of the scraper edges, the contaminants accumulated on the electrode can, for example, be scraped off from the electrode surface simultaneously at two areas each lying adjacent to one of the scraper edges, or also in two different directions of movement of stripper and electrode, such that the cleaning of the electrode is accelerated.

In another preferred embodiment, the electrode is tubular and the stripper is plate-shaped, the stripper extending round part of the circumference of the electrode.

This measure has the effect that the tubular electrode provides a coagulation surface that is as large as possible and extends about the full circumference, and at the same time the plate-shaped stripper is of small dimensions, such that it does not greatly reduce the coagulation surface area of the electrode. Thus, the coagulating action of the medical instrument is advantageously almost completely retained and is not greatly limited by the stripper. Moreover, along its plate edges extending in the longitudinal direction of the electrode carrier, the plate-shaped stripper has two scraper edges, such that the cleaning of the electrode surfaces adjoining the scraper edges is possible in each of the two directions of relative movement of the electrode and of the stripper.

In connection with the formation of the distal end of the stripper engaging around the electrode, the tubular and plate-shaped configuration of electrode and stripper, respectively, are particularly advantageous since the distal end of the stripper can be hooked on the edge of the tube opening of the distal end of the electrode and the stripper always bears on the electrode in a stable position.

In another preferred embodiment of the invention, the stripper extends round the tubular electrode with an angle range of less than approximately 60°, preferably with an angle range of less than approximately 45°, and more preferably with an angle range of less than approximately 30°.

This measure has the effect that, on the one hand, the stripper is sufficiently large to ensure rapid cleaning of the electrode surface, and, on the other hand, is still small enough that it does not unnecessarily reduce the coagulation surface area of the electrode. Therefore, the medical intervention can advantageously be carried out expeditiously.

In another preferred embodiment of the invention, the medical instrument has an outer tube at whose distal end the stripper is arranged, the electrode carrier being received in the outer tube, and the electrode carrier and the outer tube being able to be rotated relative to each other.

This measure advantageously permits a particularly compact and simple structure of the medical instrument. The outer tube surrounds the electrode carrier and protects it from damage. The relative mobility of the electrode and of the stripper is effected by the relative rotatability of the electrode carrier and of the outer tube, such that the rotation of electrode carrier and outer tube relative to each other permits the cleaning of the whole electrode surface in a short time.

In another preferred embodiment of the invention, the outer tube is rotationally fixed and the electrode carrier can rotate relative to the outer tube.

The electrode carrier in the inside of the outer tube is rotated in order to generate the relative rotation movement of the electrode and of the stripper, it being possible in particular for the electrode carrier to rotate about its longitudinal axis in both directions of rotation. This measure ensures advantageously that the outer tube remains fixed in position relative to the trocar through which the medical instrument is usually inserted into the body during the intervention, such that the cleaning of the electrode by the stripper is not subject to friction between outer tube and trocar, and, in addition, the leaktightness of the trocar is not impaired by a rotation of the outer tube. The rotation of the electrode carrier, and thus of the electrode, in the two directions of rotation advantageously results in rapid and flexible cleaning of the electrode surface, since the tissue adhering to the electrode surface can be immediately removed by corresponding rotation of the electrode by the leading scraper edge, as seen in the direction of rotation. A rotation of the electrode about an angle of 180° in both directions suffices to clean the whole electrode surface, since the semi-circumferential electrode surface, calculated from the respective scraper edge, is cleaned by the scraper edge that leads in the direction of rotation. Therefore, a complete rotation of the electrode through 360° is advantageously not necessary, which results in simpler construction of the mechanism of rotation of the medical instrument.

In another preferred embodiment of the invention, the electrode carrier is designed as suction tube.

This measure has the advantage that the medical instrument can be used not only for coagulation, but also as a suction and irrigation instrument, as a result of which blood or scraped-off tissue, for example, is sucked through the suction tube from the operating site, and the operating site can be cleaned by irrigation liquid that is transported along the electrode carrier from its proximal end to its distal end.

Further advantages and features will become clear from the following description and from the attached drawing.

It will be appreciated that the aforementioned features and the features still to be explained below can be used not only in the cited combinations, but also in other combinations or singly, without departing from the scope of the present invention.

BRIEF DESCRIPTION OF THE DRAWINGS

The invention is described and explained in greater detail below on the basis of a number of selected illustrative embodiments and with reference to the attached drawing, in which.

DETAILED DESCRIPTION OF PREFERRED EXEMPLARY EMBODIMENTS

Figure 1:
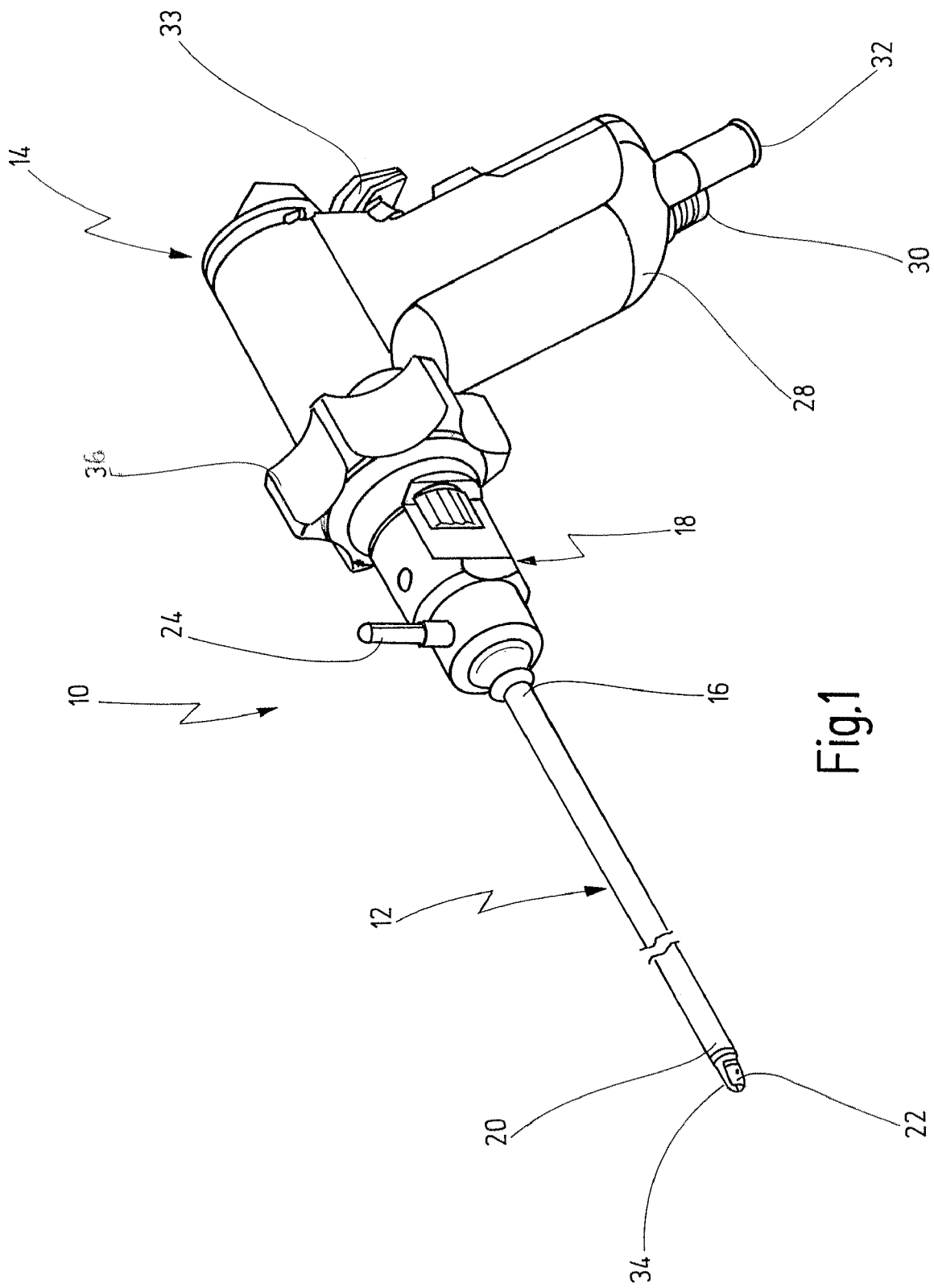
FIG. 1 shows a medical instrument according to the invention.

FIG. 1 shows a medical instrument designated by the general reference number 10. The medical instrument 10 is used in the field of minimally invasive surgery during a laparoscopy intervention for coagulating tissue in an operating site, for suctioning tissue fluid, for example, or blood from the operating site, and for irrigating the operating site.

The medical instrument 10 has a rigid shaft 12 and a handle 14. A proximal end 16 of the shaft 12 can be connected to the handle 14 via a coupling 18.

The shaft 12 has a metal electrode 22 at its distal end 20. The electrode 22 can be supplied with high-frequency current via a connector piece 24 arranged in the area of the proximal end 16 of the shaft 12. For this purpose, a high-frequency voltage source (not shown) is joined to the connector piece 24. The connector piece 24 is provided on the coupling 18 that is arranged on the proximal end 16 of the shaft 12 and that is used for connection of the shaft 12.

At its lower end 28, the handle 14 has an irrigation connector piece 30 and a suction connector piece 32 which can be connected respectively to a suction tube (not shown) and an irrigation tube (not shown). The handle 14 also has a valve actuator 33 for activating and regulating the suction current and the supply of irrigation liquid through the suction connector piece 30 and irrigation connector piece 32, respectively.

During the laparoscopy intervention, coagulated tissue can deposit itself on the electrode 22 like a crust and with a high adherence force, and this crust then fixes to the electrode 22 such that an insulating layer forms on the electrode 22 and limits further use of the medical instrument 10 or makes further use impossible. To remove this insulating layer, the medical instrument 10 has a stripper 34, which is arranged adjacent to the electrode 22 at the distal end 20 of the shaft 12. The electrode 22 and the stripper 34 can be rotated relative to each other via a rotary wheel 36 of the coupling 18 arranged at the proximal end 16 of the shaft 12.

Figure 2:
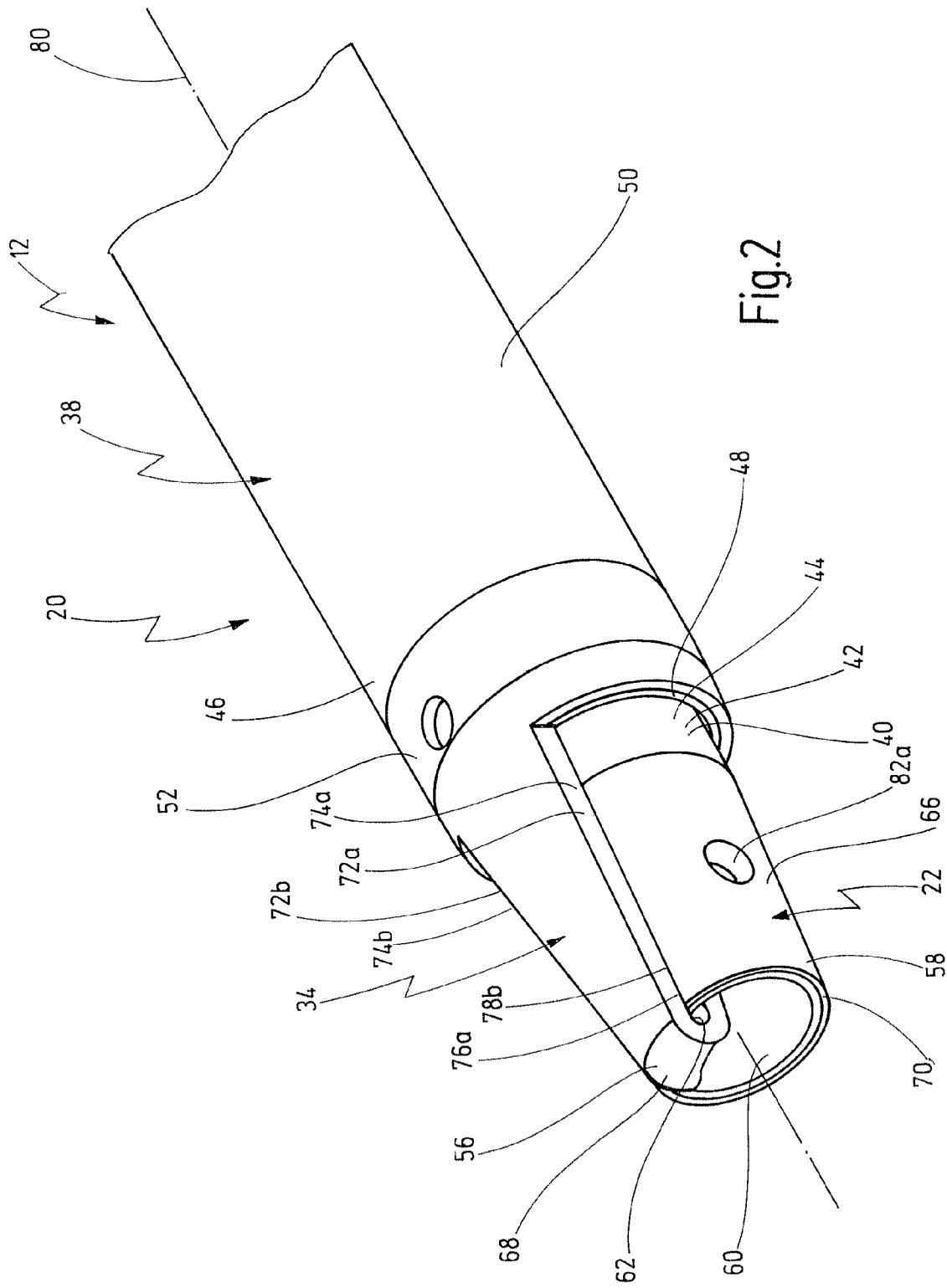
FIG. 2 shows a perspective view of a distal end of the medical instrument in FIG. 1.
Figure 3:
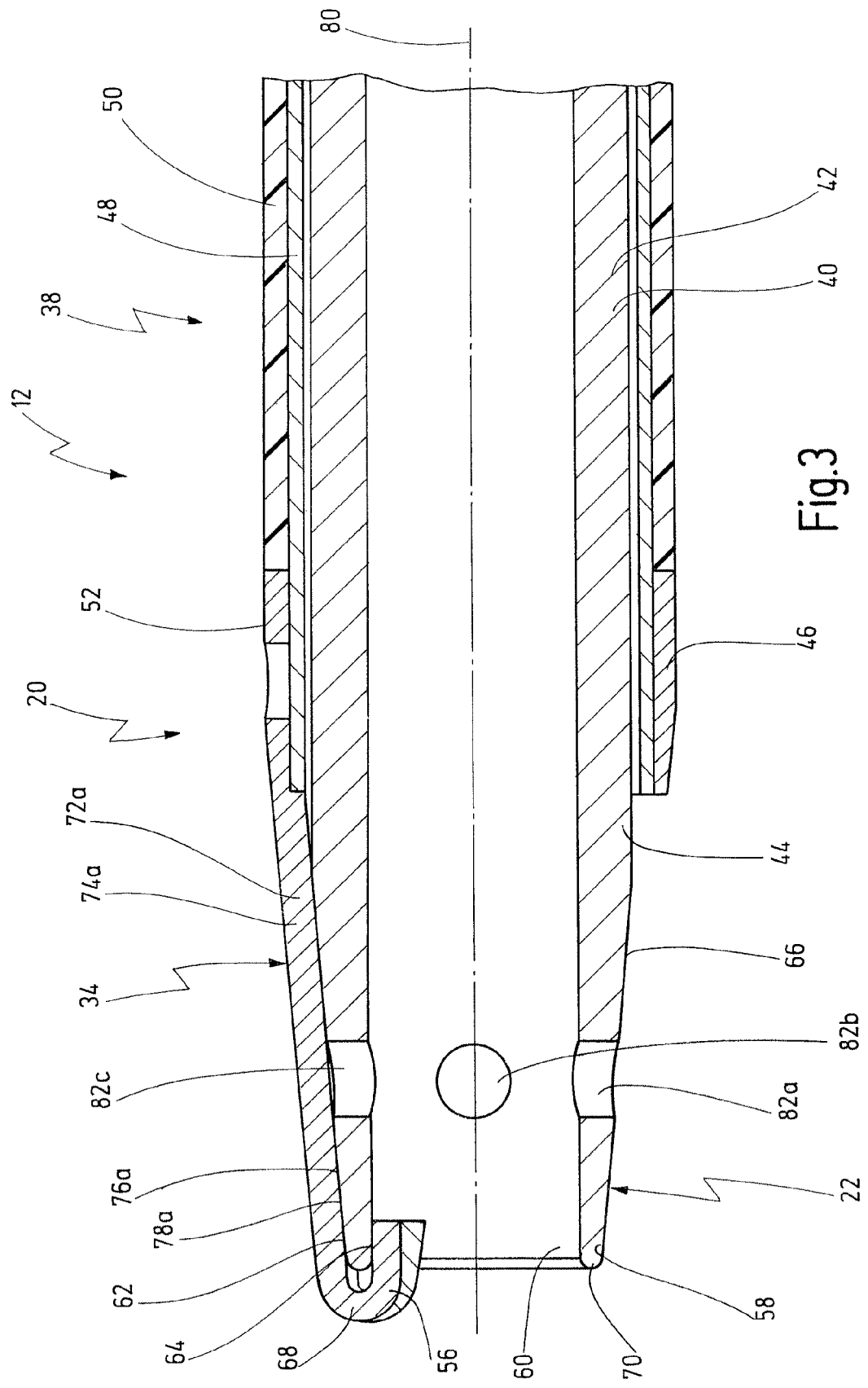
FIG. 3 shows a cross-sectional view of the distal end of the medical instrument in FIG. 1.

FIGS. 2 and 3 show a perspective view and a cross-sectional view, respectively, of the distal end 20 of the medical instrument 10. The shaft 12 of the medical instrument 10 has an outer tube 38 which surrounds a radially inner suction tube 40. The suction tube 40 serves at the same time as an electrode carrier 42 for the electrode 22. The electrode 22 is arranged at a distal end 44 of the suction tube 40, and the stripper 34 is secured on a distal end 46 of the outer tube 38. The suction tube 40 and the electrode 22 are made in one piece from metal. In the case where the suction tube 40 and the electrode 22 are not constructed in one piece, the two components can also be made of different metals. The outer tube 38 is constructed in two parts and has an inner tube 48 which is covered about its full circumference with a plastic insulation 50. The inner tube 48 of the outer tube 38 is spaced slightly apart from the suction tube 40. The outer tube 38 is shorter at the distal end than the suction tube 40, such that the electrode 22 arranged at the distal end 44 of the suction tube 40 protrudes from the outer tube 38. The stripper 34 is secured on the outer tube 38 via a proximal ring area 52 that extends about the full circumference thereof.

Figure 5A:
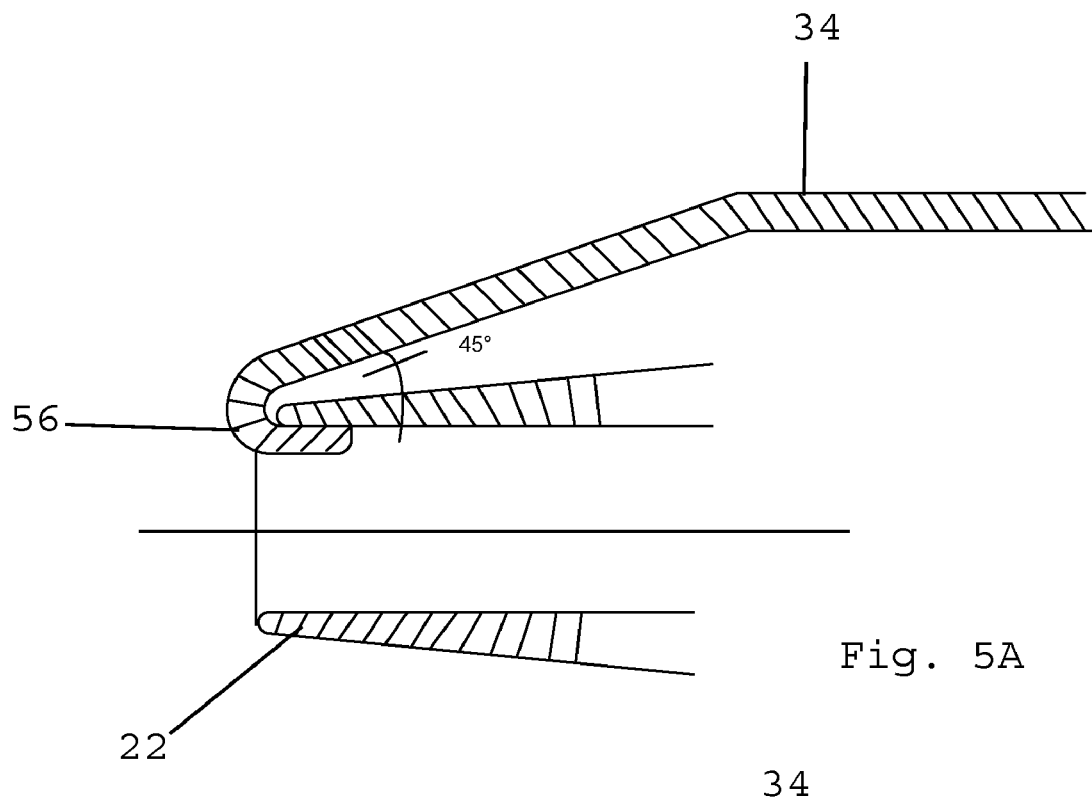
FIGS. 5A-B show cross-sectional views of the distal end of the medical instrument in FIG. 1.
Figure 5B:
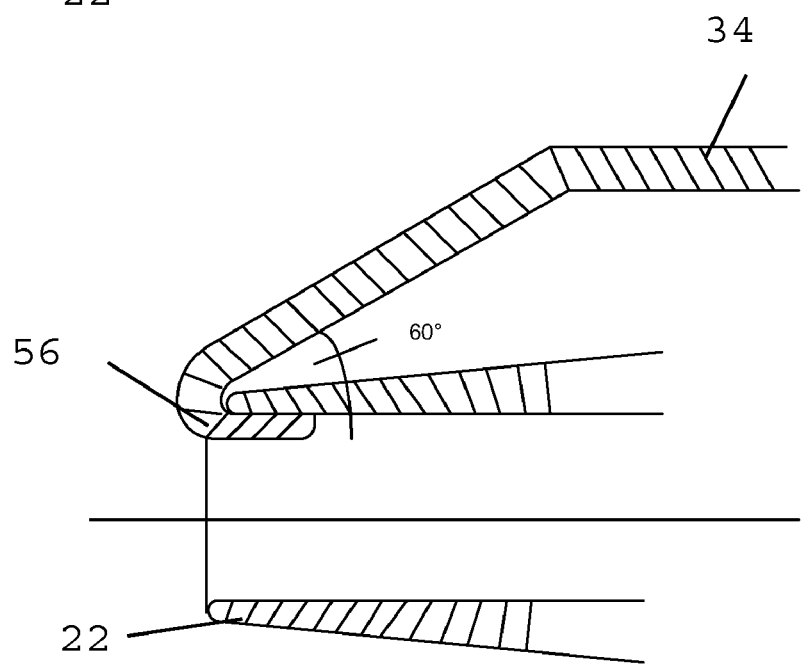

The electrode 22 is cone-shaped and tapers in the distal direction. The stripper 34 is plate-shaped, in the distal direction from its proximal ring area 52, and curves over a part of the circumference of the electrode 22 with an angle range of less than approximately 30°, for example approximately 15° around the electrode 22. The stripper 34 can preferably extend round the electrode 22 with an angle range of less than approximately 60° and more preferably with an angle range of less than approximately 45°. (See FIGS. 5A-B) The size of the stripper 34 is in this case defined by, for example, its dimensional stability under flexural and rotary stresses transverse to its longitudinal direction. This embodiment of the stripper 34 advantageously ensures that the coagulation surface area of the electrode 22 is sufficiently large and not unnecessarily reduced by the stripper 34.

A distal end 56 of the stripper 34 engages in a hook shape round a distal end 58 of the electrode 22 designed as a circular opening 60. Here, an inner face 62 of the stripper 34 in the area of its distal end 56 bears on the inner face 64 of the distal end 58 of the electrode 22. The inner face 62 of the stripper 34 directed towards the electrode 22 also touches an outer face 66 of the electrode 22 along the full longitudinal extent of the electrode 22. It is also possible for the stripper 34 and electrode 22 not to touch, and instead to be spaced apart from each other by a distance that is still suitable for maintaining the cleaning action of the stripper 34. In the area of the approximately 180° bend of the distal end 56 of the stripper 34, an outermost distal end 68 of the stripper 34 has its inner face spaced apart from a rounded edge 70 of the opening 60 of the electrode 22. The stripper 34 also tapers in the distal direction and has the shape of a curved trapezium, such that the coagulation surface of the electrode 22 also remains sufficiently large in the area of its tapering distal end 58.

The inner radius of the electrode 22 and the inner radius of the suction tube 40 are of identical dimension, such that a maximum suction power of the suction tube 40 is maintained at the distal end and sufficient irrigation liquid can be conveyed through a suction tube interior into the operating site. The outer radius of the electrode 22 decreases on account of the tapering shape of the electrode 22 in the distal direction.

Lengthwise edges 72a, 72b of the stripper 34 are designed as scraper edges 74a, 74b in order to permit removal of tissue that has accumulated on the outer face 66 of the electrode 22. The scraper edges 74a, 74b are sharp at their ends 76a, 76b facing towards the outer face 66 of the electrode 22, for example designed as blades 78a, 78b here. It is possible that only the scraper edges 74a, 74b designed as blades 78a, 78b bear on the outer face 66 of the electrode 22 or are immediately adjacent thereto, while the inner face 62 of the stripper 34 is spaced apart from the outer face 66 of the electrode 22. It is also possible for the inner face 62 of the stripper 34 to have an abrasive surface with suitable surface roughness, which permits removal of tissue adhering to the outer face 66 of the electrode 22.

The stripper 34 is made of non-conductive metal, for example. It can also be made of any other material, for example plastic, that ensures its dimensional stability under flexural and rotary stresses transverse to its longitudinal extent. It is also possible for the stripper 34 to be made of plastic and the blades 78a, 78b of metal.

The suction tube 40 and the outer tube 38 of the medical instrument 10 are designed such that they can be rotated relative to each other, with the result that the scraping action of the stripper 34 is achieved by the stripper 34 attacking the outer face 66 of the electrode 22 and carrying off the tissue or other contaminants adhering thereon. In the illustrative embodiment shown, the outer tube 38 is fixed in rotation, while the suction tube 40 can be rotated in two directions of rotation about a longitudinal axis 80 of the medical instrument 10. The longitudinal axis 80 of the medical instrument 10 corresponds to the longitudinal direction of the rigid shaft 12 of the medical instrument 10. It is also possible for the suction tube 40 to be fixed in rotation and for the outer tube 38 to rotate about the longitudinal axis 80 of the medical instrument 10.

A rotary movement of the suction tube 40 is effected via the manually actuated rotary wheel 36 which is arranged at the proximal end 16 of the shaft 12 and which the user manoeuvres. The spaced arrangement of the suction tube 40 and of the inner tube 48 of the outer tube 38 ensures that the rotary movement of the suction tube 40 about the longitudinal axis 80 of the medical instrument 10 is not impaired by additional frictional forces between bearing surfaces of the suction tube 40 and of the outer tube 38.

In its outer face 66, the electrode 22 also has four openings 82. Of these, FIG. 3 shows three openings 82a-82c arranged at 90° to one another. The openings 82 allow liquid or tissue situated to the sides of the electrode 22 to be suctioned off in the proximal direction. The irrigation liquid can also flow out through the openings 82 and irrigate the operating site laterally of the electrode 22. The irrigation liquid flowing out also wets the outer face 66 of the electrode 22 and can soften and loosen the contaminants on the outer face 66 of the electrode 22, such that the scraping-off of the contaminants by the stripper 34 is assisted and can be done more easily. When the electrode 22 is rotated about the longitudinal axis 80 of the medical instrument 10, the irrigation liquid comes into contact with the outer face 66 of the electrode 22 lying adjacent to the respective opening 82 and counter to the direction of rotation of the suction tube 40, such that the contaminants adhering there are loosened before this face with the loosened tissue turns towards the respective leading scraper edge 74a, 74b, seen in the direction of rotation, and the tissue is scraped off by the blade 78a, 78b. If the irrigation liquid flows out in particular through one of the openings 82 situated in the area of the stripper 34, the emerging irrigation liquid reduces the friction arising between the inner face 62 of the stripper 34 and the outer face 66 of the electrode 22, as a result of which wear of the material of the electrode 22 and of the stripper 34 is reduced.

Figure 4:
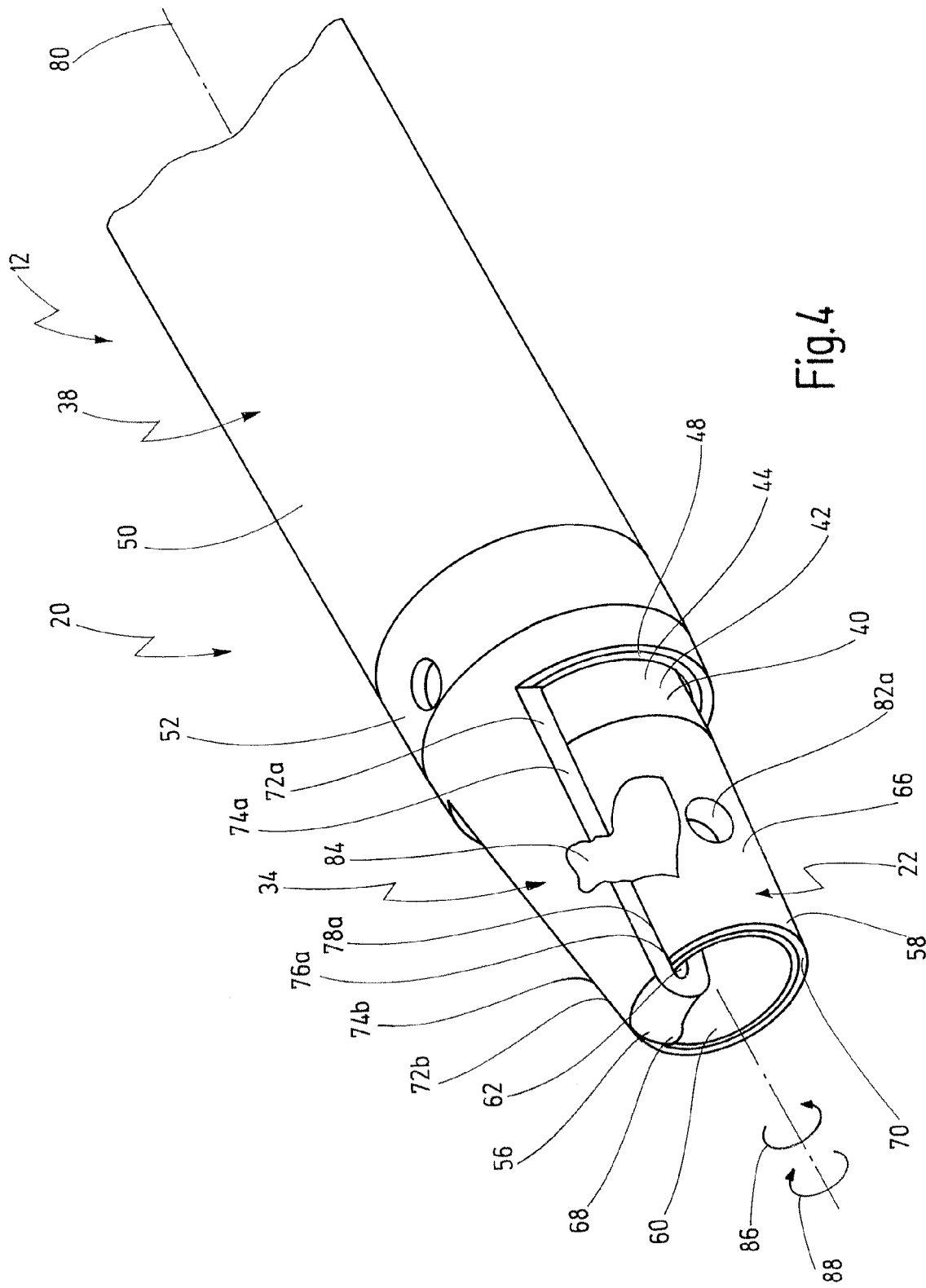
FIG. 4 shows another perspective view of the distal end of the medical instrument in FIG. 1.

FIG. 4 shows the distal end 20 of the shaft 12 of the medical instrument 10 during operation. The contaminant designated by reference number 84, and in the form of a crust adhering to the outer face 66 of the electrode 22, is removed by rotation of the suction tube 40 about the longitudinal axis 80 of the medical instrument 10 along an arrow 86. The blade 78a at the lower end 76a of the scraper edge 74a engages the tissue 84 and lifts it from the outer face 66 of the electrode 22, along the direction of rotation of the arrow 86. As is shown in FIG. 4, the partially scraped-off tissue 84 can place itself over the stripper 34 before it is completely detached from the outer face 66 of the electrode 22 and drops from the stripper 34 and is then suctioned off through the suction tube 40.

The electrode 22 can also be rotated along an arrow 88 about the longitudinal axis 80 of the medical instrument 10, such that the tissue located adjacent to the scraper edge 74b is removed from the outer face 66 of the electrode 22.

The turning of the electrode 22 through an angle of rotation of 180° about the longitudinal axis 80 of the medical instrument 10 leads to a cleaning of half the circumference of the outer face 66 of the electrode 22 by the scraper edge 74a, 74b, as a result of which removal of the contaminants 84 from the whole outer face 66 of the electrode is achieved by turning the electrode 22 in each case through approximately 180° in both directions of rotation 86, 88. The presence of the two scraper edges 74a, 74b means in particular that it is not necessary to rotate the electrode 22 through an angle of 360° about the longitudinal axis 80 in order for the contaminants 84, which are adjacent to one of the scraper edges 74a, 74b, to be removed by the respective other scraper edge 74a, 74b.

What is claimed is:

1. A medical instrument for coagulation of tissue, comprising an electrode carrier having a distal end, an electrode arranged at said distal end of said electrode carrier, and which can be supplied with high-frequency current, and a stripper arranged directly adjacent to said electrode, said stripper and said electrode being able to be moved relative to each other in order to remove contaminants from said electrode wherein said electrode is tubular and has a tube opening a distal end of said electrode, and said stripper engages around said distal end into said tube opening.

2. The instrument of claim 1, wherein said stripper and said electrode are movable relative to each other transverse to a longitudinal direction of said electrode carrier.

3. The instrument of claim 1, wherein said stripper extends in a longitudinal direction of said electrode at least along a partial area of said electrode.

4. The instrument of claim 1, wherein said stripper tapers in distal direction, 5. The instrument of claim 1, wherein said stripper engages around said distal end of said electrode into said tube opening in hook-shaped fashion.

6. The instrument of claim 1, wherein said stripper has a scraper edge facing towards said electrode and designed as a blade.

7. The instrument of claim 1, wherein said stripper has two scraper edges facing towards said electrode and each designed as a blade.

8. The instrument of claim 1, wherein said stripper is blade-shaped, said stripper extending around part of a circumference of said electrode.

9. The instrument of claim 8, wherein said stripper extends around said tubular electrode with an angle range of less than approximately 60°.

10. The instrument of claim 9, wherein said stripper extends around said tubular electrode with an angle range of less than approximately 45°.

11. The instrument of claim 9, wherein said stripper extends around said tubular electrode with an angle range of less than approximately 30°.

12. The instrument of claim 1, further comprising an outer tube at whose distal end said stripper is arranged, said electrode carrier being received in said outer tube, and said electrode carrier and said outer tube being able to be rotated relative to each other.

13. The instrument of claim 12, wherein said outer tube is rotationally fixed and said electrode carrier can be rotated relative to said outer tube.

14. The instrument of claim 1, wherein said electrode carrier is designed as a suction tube.

* * * * *